United States Patent
Bui et al.

(10) Patent No.: US 8,697,039 B2
(45) Date of Patent: Apr. 15, 2014

(54) COMPOSITIONS CONTAINING SILICONE POLYMER, WAX AND VOLATILE SOLVENT

(75) Inventors: Hy Si Bui, Piscataway, NJ (US); Shao Xiang Lu, Plainsboro, NJ (US); Wei Hong Yu, Edison, NJ (US); Francois Pradier, New York, NY (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/852,093

(22) Filed: Aug. 6, 2010

(65) Prior Publication Data

US 2010/0297050 A1  Nov. 25, 2010

Related U.S. Application Data

(63) Continuation of application No. 11/217,293, filed on Sep. 2, 2005, now Pat. No. 7,790,148.

(51) Int. Cl.
*A61Q 1/06* (2006.01)
*A61Q 1/04* (2006.01)
*A61Q 1/08* (2006.01)

(52) U.S. Cl.
USPC ............ 424/64; 424/69; 424/78.03; 424/401

(58) Field of Classification Search
None
See application file for complete search history.

(56) References Cited

U.S. PATENT DOCUMENTS

| | | | |
|---|---|---|---|
| 2,823,195 A | 2/1958 | Shorr et al. | |
| 2,823,218 A | 2/1958 | Speier et al. | |
| 3,723,566 A | 3/1973 | Thompson et al. | |
| 4,322,400 A | 3/1982 | Yuhas | |
| 4,822,852 A | 4/1989 | Wittmann et al. | |
| 5,262,505 A | 11/1993 | Nakashima et al. | |
| 5,407,986 A | 4/1995 | Furukawa et al. | |
| 5,412,004 A | 5/1995 | Tachibana et al. | |
| 5,473,041 A | 12/1995 | Itoh | |
| 5,512,272 A | 4/1996 | Krzysik | |
| 5,556,613 A | 9/1996 | Arnaud et al. | |
| 5,567,428 A | 10/1996 | Hughes | |
| 5,725,882 A | 3/1998 | Kumar et al. | |
| 5,750,095 A | 5/1998 | Arnaud et al. | |
| 5,837,223 A | 11/1998 | Barone et al. | |
| 5,874,069 A | 2/1999 | Mendolia et al. | |
| 5,919,441 A | 7/1999 | Mendolia et al. | |
| 5,969,172 A | 10/1999 | Nye | |
| 5,981,680 A | 11/1999 | Petroff et al. | |
| 5,985,297 A | 11/1999 | Mellul et al. | |
| 6,045,782 A | 4/2000 | Krog et al. | |
| 6,051,216 A | 4/2000 | Barr et al. | |
| 6,060,072 A | 5/2000 | Konik et al. | |
| 6,103,250 A | 8/2000 | Brieva et al. | |
| 6,177,091 B1 | 1/2001 | Bara et al. | |
| 6,326,012 B1 | 12/2001 | Arnaud et al. | |
| 6,353,076 B1 | 3/2002 | Barr et al. | |
| 6,362,287 B1 | 3/2002 | Chorvath et al. | |
| 6,362,288 B1 | 3/2002 | Brewer et al. | |
| 6,376,078 B1 | 4/2002 | Inokuchi | |
| 6,423,324 B1 | 7/2002 | Murphy et al. | |
| 6,426,062 B1 | 7/2002 | Chopra et al. | |
| 6,451,295 B1 | 9/2002 | Cai et al. | |
| 6,503,632 B1 | 1/2003 | Hayashi et al. | |
| 6,524,598 B2 | 2/2003 | Sunkel et al. | |
| 6,541,017 B1 | 4/2003 | Lemann et al. | |
| 6,569,955 B1 | 5/2003 | Brewer et al. | |
| 6,682,748 B1 | 1/2004 | De La Poterie et al. | |
| 6,843,982 B1 | 1/2005 | Arnaud et al. | |
| 6,916,464 B2 | 7/2005 | Hansenne et al. | |
| 7,790,148 B2 * | 9/2010 | Bui et al. ...................... | 424/64 |
| 2002/0028223 A1 | 3/2002 | Vatter et al. | |
| 2002/0048557 A1 | 4/2002 | Cai et al. | |
| 2002/0051758 A1 | 5/2002 | Cai et al. | |
| 2003/0068348 A1 | 4/2003 | Ferrari et al. | |
| 2003/0072730 A1 | 4/2003 | Tournilhac | |
| 2003/0082129 A1 | 5/2003 | Buckingham et al. | |
| 2003/0170188 A1 | 9/2003 | Ferrari et al. | |
| 2003/0228333 A1 | 12/2003 | Fecht et al. | |
| 2003/0232030 A1 | 12/2003 | Lu et al. | |
| 2003/0235548 A1 | 12/2003 | Lu et al. | |
| 2003/0235552 A1 | 12/2003 | Yu | |
| 2003/0235553 A1 | 12/2003 | Lu et al. | |
| 2004/0001799 A1 | 1/2004 | Lu et al. | |
| 2004/0115153 A1 | 6/2004 | Yu | |
| 2004/0115154 A1 | 6/2004 | Yu | |
| 2004/0120912 A1 | 6/2004 | Yu | |

(Continued)

FOREIGN PATENT DOCUMENTS

| | | |
|---|---|---|
| EP | 0 377 447 A2 | 7/1990 |
| EP | 0 594 285 A2 | 4/1994 |

(Continued)

OTHER PUBLICATIONS

Dow Corning® 2-8178 Gellant, Ref. No. 27/1055-01, Aug. 2002, 35 pp.

Dow Corning® 2-8178 Gellant, Product Information Personal Care, 6 pp., Aug. 13, 2002.

Shin-Etsu Silicones for Personal Care; Product Brochure, KSP-100•101•102•103•104•105 "Hybrid Silicone Powders for Personal Care" 2000.

Shin-Etsu Silicones for Personal Care; Product Brochure, KSP-200•300 "Hybrid Silicone Powders containing Fluoroalkyl or Phenyl group for Personal Care" 2001.

Dow Corning 2-8178 Gellant, Ref. No. 27-1055B-01, Apr. 16, 2003, 6 pp.

Notice of Rejection for Japanese Patent Application 2004-512707 issued Jun. 6, 2006 (w/English Translation).

*Primary Examiner* — Jyothsna Venkat
(74) *Attorney, Agent, or Firm* — Oblon, Spivak, McClelland, Maier & Neustadt, L.L.P.

(57) ABSTRACT

The invention relates to compositions containing at least one polyorganosiloxane-containing polymer, at least one volatile non-silicone oil, at least one alkylene polymer wax, at least one silicone film-forming agent and, optionally, at least one long-chain alcohol wax, at least one coloring agent, and/or at least one volatile silicone oil, as well as to methods for using such compositions and to kits containing such compositions.

6 Claims, No Drawings

(56) References Cited

U.S. PATENT DOCUMENTS

| | | | |
|---|---|---|---|
| 2004/0126336 A1 | 7/2004 | Hansenne et al. | |
| 2004/0170586 A1 | 9/2004 | Ferrari et al. | |
| 2004/0180032 A1 | 9/2004 | Manelski et al. | |
| 2004/0197285 A1 | 10/2004 | Van Dort | |
| 2004/0223936 A1 | 11/2004 | Fecht et al. | |
| 2005/0009989 A1 | 1/2005 | Liew et al. | |
| 2005/0020769 A1 | 1/2005 | Lu et al. | |
| 2005/0089492 A1 | 4/2005 | Lu et al. | |
| 2005/0158260 A1 | 7/2005 | Ferrari et al. | |
| 2008/0171008 A1 | 7/2008 | Bui | |

FOREIGN PATENT DOCUMENTS

| | | |
|---|---|---|
| EP | 0 693 517 A1 | 1/1996 |
| EP | 0 709083 | 5/1996 |
| EP | 0 923 928 | 6/1999 |
| EP | 0 979 643 | 2/2000 |
| EP | 1 048 686 | 11/2000 |
| EP | 1 068 856 | 1/2001 |
| EP | 1 266 647 | 12/2002 |
| EP | 1 266 648 | 12/2002 |
| FR | 2 715 294 | 7/1995 |
| FR | 2 765 800 | 1/1999 |
| GB | 134 8783 | 3/1974 |
| JP | 02-25411 | 1/1990 |
| JP | 06-279253 | 10/1994 |
| JP | 08-239316 | 10/1994 |
| JP | 09-071505 | 3/1997 |
| JP | 11-236314 | 8/1999 |
| JP | 2001-081009 | 3/2001 |
| JP | 2001-503070 | 3/2001 |
| WO | WO 97/36572 | 10/1997 |
| WO | WO 97/36573 | 10/1997 |
| WO | WO 99/47111 | 1/1999 |
| WO | WO 99/06473 | 2/1999 |
| WO | WO99/22710 | 5/1999 |
| WO | WO 01/09239 A1 | 2/2001 |
| WO | WO 01/97758 A2 | 12/2001 |
| WO | WO 02/17870 A2 | 3/2002 |
| WO | WO 02/17871 A2 | 3/2002 |
| WO | WO 02/089760 A1 | 11/2002 |
| WO | WO 03/013447 A2 | 2/2003 |
| WO | WO 03/105788 A2 | 6/2003 |
| WO | WO 03/101412 A2 | 12/2003 |
| WO | WO 2004/054523 | 7/2004 |
| WO | WO 2004/054524 | 7/2004 |

* cited by examiner

COMPOSITIONS CONTAINING SILICONE POLYMER, WAX AND VOLATILE SOLVENT

CROSS-REFERENCE TO RELATED APPLICATIONS

This application is a continuation of U.S. application Ser. No. 11/217,293, filed Sep. 2, 2005, the entire contents of which are hereby incorporated by reference.

FIELD OF THE INVENTION

The present invention relates to compositions comprising at least one polyorganosiloxane-containing polymer, at least one volatile non-silicone oil, at least one alkylene polymer wax, at least one silicone film-forming agent and, optionally, at least one long-chain alcohol wax, at least one coloring agent, and/or at least one volatile silicone oil, as well as to methods for using such compositions and to kits containing such compositions.

DISCUSSION OF THE BACKGROUND

Many pigmented cosmetic compositions such as foundations, lipsticks and mascaras have been developed for longer wear and transfer resistance properties. This is typically accomplished by the use of ingredients that form a film after application, ingredients such as silicone film forming agents. Such compositions generally contain volatile solvents which evaporate on contact with the skin or other keratinous tissue, leaving behind a film or layer comprising waxes and/or resins, pigments, fillers, and actives.

In the past, it has been problematic to formulate compositions containing silicone film forming agents such as silicone resins into compositions possessing acceptable cosmetic properties such as, for example, acceptable wear, transfer-resistance, feel, spreadability and stability properties, particularly where the composition was a solid composition such as a lipstick or a stick foundation.

Thus, there remains a need for improved compositions containing silicone film forming agents such as silicone resins, particularly solid compositions containing such silicone film-forming agents, which have acceptable or improved wear, transfer-resistance, feel, spreadability and/or stability properties for application to keratin materials such as skin, lips or eyelashes.

Accordingly, one aspect of the present invention is to provide a care and/or makeup and/or treatment composition for keratinous material such as the skin, hair and/or lips, which is able to address or overcome at least one of the aforementioned problems with the prior art compositions, as well as to provide methods for using such compositions and kits containing such compositions.

SUMMARY OF THE INVENTION

The present invention relates to compositions, preferably long wearing or transfer-resistant make-up compositions, comprising at least one polyorganosiloxane-containing polymer, at least one volatile non-silicone oil, at least one alkylene polymer wax and at least one silicone film forming agent. Preferably, the compositions further comprise at least one long-chain alcohol wax, at least one coloring agent, and/or at least one volatile silicone oil. Most preferably, the compositions further comprise both at least one coloring agent and at least one long-chain alcohol wax.

The present invention also relates to methods of treating, caring for and/or making up keratinous material (for example, skin) by applying compositions of the present invention to the keratinous material in an amount sufficient to treat, care for and/or make up the keratinous material.

The present invention further relates to covering or hiding skin defects associated with keratinous material (for example, skin) by applying compositions of the present invention to the keratinous material in an amount sufficient to cover or hide such skin defects.

The present invention also relates to methods of enhancing the appearance of keratinous material (for example, skin) by applying compositions of the present invention to the keratinous material in an amount sufficient to enhance the appearance of the keratinous material.

The present invention further relates to compositions having improved cosmetic properties such as, for example, improved long wear, transfer resistance and/or waterproof properties. The compositions may also possess improved flexibility, wearability, drying time and/or retention as well as reduced tackiness and/or migration over time.

The present invention also relates to kits comprising a composition, preferably a long wearing or transfer-resistant make-up composition, comprising at least one polyorganosiloxane-containing polymer, at least one volatile non-silicone oil, at least one alkylenene polymer wax and at least one silicone film forming agent, preferably further comprising at least one coloring agent, at least one volatile silicone oil and/or at least one long-chain alcohol wax. Such kits can also include additional compositions such as, for example, topcoats for application to long wearing or transfer resistant make-up compositions or primers (basecoats) for application to keratin materials prior to application of a long wearing or transfer resistant make-up composition.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

"Film former" or "film forming agent" as used herein means a polymer that, after dissolution in at least one solvent, leaves a film on the substrate to which it is applied, for example, once the at least one solvent evaporates, absorbs and/or dissipates on the substrate.

"Transfer resistance" as used herein refers to the quality exhibited by compositions that are not readily removed by contact with another material, such as, for example, a glass, food, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human lips followed by "kissing" a material, for example, a sheet of paper, after expiration of a certain amount of time following application, such as 2 minutes after application. Similarly, transfer resistance of a composition may be evaluated by the amount of product transferred from a wearer to any other substrate, such as transfer from the neck of an individual to a collar after the expiration of a certain amount of time following application. The amount of composition transferred to the substrate (e.g., collar, or paper) may then be evaluated and compared. For example, a composition may be transfer resistant if a majority of the product is left on the wearer, e.g., lips, neck, etc. Further, the amount transferred may be compared with that transferred by other compositions, such as commercially available compositions. In a preferred embodiment of the present invention, little or no composition is transferred to the substrate. Thus, transfer-resistant compositions include transfer-free compositions.

"Long wear" compositions as used herein, refers to compositions where at least one property chosen from consistency, texture, and color remains the same as at the time of application, as viewed by the naked eye, after an extended period of time, such as, for example, 1 hour, 2 hours, and further such as 8 hours. Long wear properties may be evaluated by any method known in the art for evaluating such properties. For example, long wear may be evaluated by a test involving the application of a composition to human skin (including lips) and evaluating the consistency, texture and color of the composition after an extended period of time. For example, the consistency, texture and color of a lip composition may be evaluated immediately following application and these characteristics may then be re-evaluated and compared after an individual has worn the lip composition for a certain amount of time. Further, these characteristics may be evaluated with respect to other compositions, such as commercially available compositions.

"Make-up composition" as used herein means any composition applied to keratin materials for aesthetic purposes. Examples of acceptable make-up compositions include, but are not limited to, lip compositions such as lipsticks, liquid lip colors, lip glosses, skin compositions such as stick foundations or compact foundations, fingernail compositions such as nail polish and eyelash/hair compositions such as mascaras.

The compositions, kits and methods of the present invention can comprise, consist of, or consist essentially of the essential elements and limitations of the invention described herein, as well as any additional or optional ingredients, components, or limitations described herein or otherwise useful in personal care compositions intended for topical application to keratin materials.

The compositions of the present invention may be in any form. For example, they may be a paste, a solid, a gel, or a cream. They may be an emulsion, such as an oil-in-water or water-in-oil emulsion, a multiple emulsion, such as an oil-in-water-in-oil emulsion or a water-in-oil-in-water emulsion, or a solid, rigid or supple gel, including anhydrous gels. The compositions can also be in a form chosen from a translucent anhydrous gel and a transparent anhydrous gel. The compositions of the invention may, for example, comprise an external or continuous fatty phase. The compositions may be anhydrous. In another embodiment, the compositions of the invention may be transparent or clear. The compositions can also be a molded composition or cast as a stick or a dish. The compositions in one embodiment can be a solid such as a molded stick or a poured stick. The composition can be either solid (for example, a lipstick, a stick foundation or a compact foundation) or liquid (for example, a liquid lip composition, mascara, liquid foundation or nail polish). Also, the composition can contain water, but it also may be anhydrous, if desired.

According to preferred embodiments of the present invention, the compositions are solid. The solid nature of the compositions can be determined by determining the hardness of the compositions. The hardness of a composition may, for example, be expressed in gramforce (gf). Solid compositions of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

When the compositions are solid, the hardness of the composition of the present invention is such that the compositions are self-supporting but can easily form a satisfactory deposit on a keratinous material. In addition, this hardness imparts good impact strength to the inventive compositions, which can be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 40° C., 37° C., 45° C., 50° C. and under freeze-thaw conditions. A composition is considered to lack stability if in any of these tests an abnormality that impedes functioning of the composition is observed. The skilled artisan will readily recognize an abnormality that impedes functioning of a composition based on the intended application.

In accordance with preferred embodiments of the present invention, compositions comprising at least one polyorganosiloxane-containing polymer, at least one volatile non-silicone oil, at least one alkylene polymer wax and at least one silicone film forming agent are provided.

Polyorganosiloxane-Containing Polymer

According to preferred embodiments, the composition comprises a polyorganosiloxane-containing polymer. Any polyorganosiloxane-containing polymer can be used. For example, suitable polyorganosiloxane-containing polymers include, but are not limited to, the polyorganosiloxane-containing polymers and copolymers disclosed in U.S. patent application publication no. 2004-0170586, corresponding to U.S. patent application Ser. No. 10/733,467, filed Dec. 10, 2003, hereby incorporated by reference in its entirety.

Preferably, the polyorganosiloxane containing polymer or copolymer is a polysilicone polyamide polymer such as, for example, those disclosed in U.S. Pat. Nos. 5,874,069, 5,919,441, 6,051,216 and 5,981,680, all of which are hereby incorporated by reference in their entirety, and/or those polymers described below.

Preferred polyorganosiloxane containing polymers are chosen from homopolymers and copolymers, preferably, with a weight-average molecular mass ranging from about 500 to about $2.5 \times 10^6$ or more, comprising at least one moiety comprising: at least one polyorganosiloxane group comprising, preferably, from 1 to about 10,000 organosiloxane units in the chain of the moiety or in the form of a graft, and at least two groups capable of establishing hydrogen interactions.

According to preferred embodiments of the present invention, the polyorganosiloxane-containing polymers used in the composition of the invention may belong to the following two families:

a) polyorganosiloxanes comprising at least two groups capable of establishing hydrogen interactions, these two groups being located in the polymer chain; and/or b) polyorganosiloxanes comprising at least two groups capable of establishing hydrogen interactions, these two groups being located on grafts or branches.

The polyorganosiloxane containing polymers of the present invention can be liquid or solid at room temperature. Preferably, the polymers are solid. When the polymers are solid, it is preferable that they can be dissolved before or during use in a solvent with hydrogen interaction capable of breaking the hydrogen interactions of the polymers, for instance $C_2$ to $C_8$ lower alcohols and especially ethanol, n-propanol or isopropanol. It is also possible to use these hydrogen interaction "breaking" solvents as co-solvents in the compositions of the present invention. These solvents may then be stored in the composition or may be removed by selective evaporation, which is well known to those skilled in the art.

The polymers comprising two groups capable of establishing hydrogen interactions in the polymer chain may be polymers comprising at least one moiety corresponding to the formula:

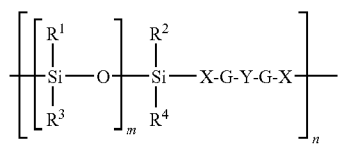

(I)

in which:

1) $R^1$, $R^2$, $R^3$ and $R^4$, which may be identical or different, represent a group chosen from:

linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms, $C_6$ to $C_{10}$ aryl groups, optionally substituted with one or more $C_1$ to $C_4$ alkyl groups, polyorganosiloxane chains possibly containing one or more oxygen, sulphur and/or nitrogen atoms;

2) the groups X, which may be identical or different, represent a linear or branched $C_1$ to $C_{30}$ alkylenediyl group, possibly containing in its chain one or more oxygen and/or nitrogen atoms;

3) Y is a saturated or unsaturated, $C_1$ to $C_{50}$ linear or branched divalent alkylene, arylene, cycloalkylene, alkylarylene or arylalkylene group, possibly comprising one or more oxygen, sulphur and/or nitrogen atoms, and/or bearing as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or 4) Y represents a group corresponding to the formula:

in which

T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from 0, N and S, or T represents a trivalent atom chosen from N, P and Al, and $R^5$ represents a linear or branched $C_1$ to $C_{50}$ alkyl group or a polyorganosiloxane chain, possibly comprising one or more ester, amide, urethane, thiocarbamate, urea, thiourea and/or sulphonamide groups, which may be linked to another chain of the polymer;

5) the groups G, which may be identical or different, represent divalent groups chosen from:

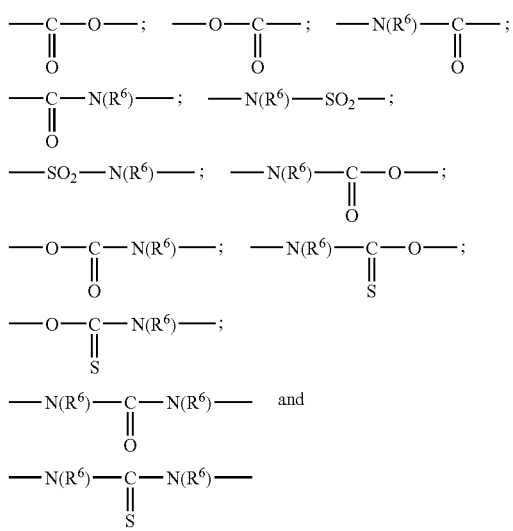

in which $R^6$ represents a hydrogen atom or a linear or branched $C_1$ to $C_{20}$ alkyl group, on condition that at least 50% of the groups $R^6$ of the polymer represents a hydrogen atom and that at least two of the groups G of the polymer are a group other than:

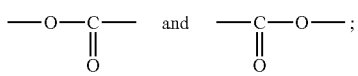

6) n is an integer of at least 1, for example ranging from 2 to 500 and preferably from 2 to 200, and m is an integer of at least one, ranging from 1 to 35,000, for example, from 1 to 10,000 and 1 to 2,500, from 1 to 700 and from 6 to 200, including all values and subranges there between.

According to the invention, 80% of the groups $R^1$, $R^2$, $R^3$ and $R^4$ of the polymer are preferably chosen from methyl, ethyl, phenyl and 3,3,3-trifluoropropyl groups.

According to the invention, Y can represent various divalent groups, furthermore optionally comprising one or two free valencies to establish bonds with other moieties of the polymer or copolymer. Preferably, Y represents a group chosen from:

a) linear $C_1$ to $C_{20}$ and preferably $C_1$ to $C_{10}$ alkylene groups,
b) $C_{30}$ to $C_{56}$ branched alkylene groups possibly comprising rings and unconjugated unsaturations,
c) $C_5$-$C_6$ cycloalkylene groups,
d) phenylene groups optionally substituted with one or more $C_1$ to $C_{40}$ alkyl groups,
e) $C_1$ to $C_{20}$ alkylene groups comprising from 1 to 5 amide groups,
f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups,
g) polyorganosiloxane chains of formula:

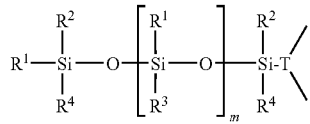

in which $R^1$, $R^2$, $R^3$, $R^4$, T and m are as defined above, and
h) polyorganosiloxane chains of formula:

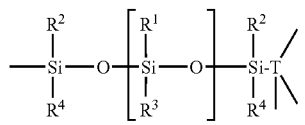

The polyorganosiloxanes of the second family may be polymers comprising at least one moiety corresponding to formula (II):

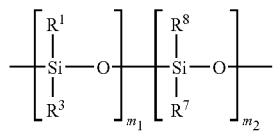

(II)

in which
$R^1$ and $R^3$, which may be identical or different, are as defined above for formula (I),
$R^7$ represents a group as defined above for $R^1$ and $R^3$, or represents a group of formula —X-G-$R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^8$ represents a group of formula —X-G-$R^9$ in which X, G and $R^9$ are as defined above, $m_1$ is an integer of at least one ranging from 1 to 35,000, for example, from 1 to 10,000 and 1 to 2,500, from 1 to 700, and from 6 to 200, including all values and subranges there between; and $m_2$ is an integer of at least one ranging from 1 to 35,000, for example, from 1 to 10,000 and 1 to 2,500, from 1 to 700, and from 6 to 200, including all values and subranges there between.

According to the invention, the polyorganosiloxane containing polymer may be a homopolymer, that is to say a polymer comprising several identical moieties, in particular moieties of formula (I) or of formula (II).

According to the invention, it is also possible to use a polymer consisting of a copolymer comprising several different moieties of formula (I), that is to say a polymer in which at least one of the groups $R^1$, $R^2$, $R^3$, $R^4$, X, G, Y, m and n is different in one of the moieties. The copolymer may also be formed from several moieties of formula (II), in which at least one of the groups $R^1$, $R^3$, $R^7$, $R^8$, $m_1$ and $m_2$ is different in at least one of the moieties.

It is also possible to use a copolymer comprising at least one moiety of formula (I) and at least one moiety of formula (II), the moieties of formula (I) and the moieties of formula (II) possibly being identical to or different from each other.

According to preferred embodiments, it is also possible to use a copolymer comprising at least one hydrocarbon-based moiety comprising two groups capable of establishing hydrogen interactions, chosen from ester, amide, sulphonamide, carbamate, thiocarbamate, urea and thiourea groups, and combinations thereof.

These copolymers may be block copolymers or grafted copolymers.

According to a first embodiment of the invention, the groups capable of establishing hydrogen interactions are amide groups of formulae —C(O)NH— and —HN—C(O)—.

In this case, the polymer may comprise at least one moiety of formula (III) or (IV):

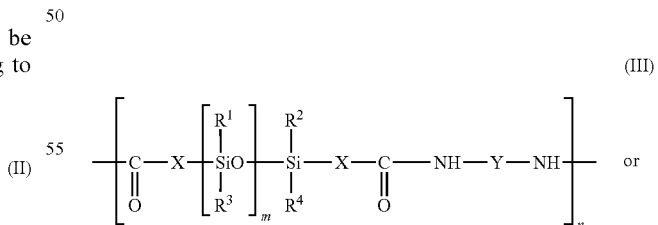

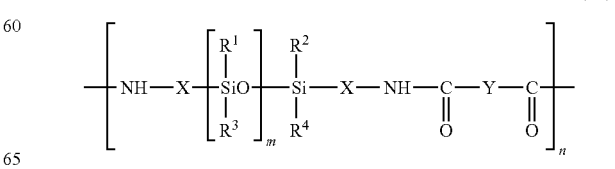

in which $R^1$, $R^2$, $R^3$, $R^4$, X, Y, m and n are as defined above.

Such a moiety may be obtained:
either by a condensation reaction between a silicone containing □,ω-carboxylic acid ends and one or more diamines, according to the following reaction scheme:

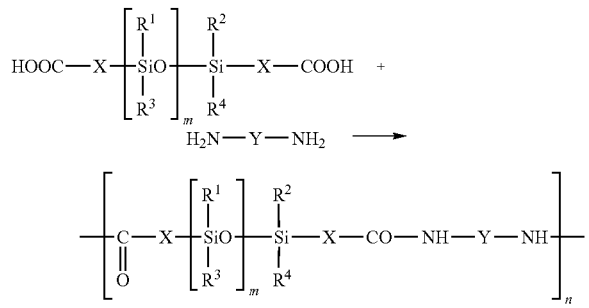

or by reaction of two molecules of □-unsaturated carboxylic acid with a diamine according to the following reaction scheme:

CH$_2$=CH—X$^1$—COOH+H$_2$N—Y—NH$_2$→CH$_2$=CH—X$^1$—CO—NH—Y—NH—CO—X$^1$—CH=CH$_2$ followed by the addition of a siloxane to the ethylenic unsaturations, according to the following scheme:

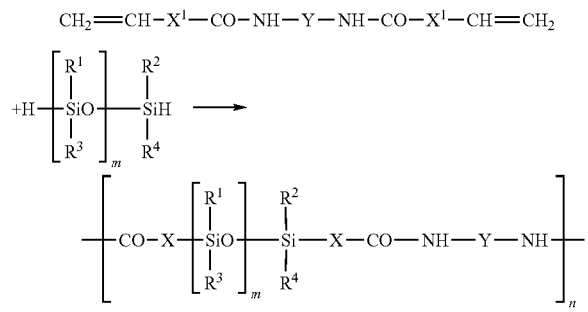

in which X$^1$—(CH$_2$)$_2$— corresponds to X defined above and Y, R$^1$, R$^2$, R$^3$, R$^4$ and m are as defined above;
or by reaction of a silicone containing ϵ,ω-NH$_2$ ends and a diacid of formula HOOC—Y—COOH according to the following reaction scheme:

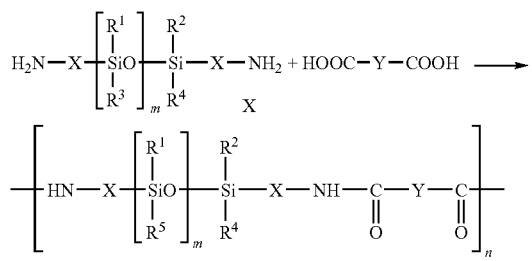

In these polyamides of formula (III) or (IV), m is an integer of at least one as defined above, and preferably in the range from 1 to 700, for example, from 15 to 500 and from 15 to 45, including all values and subranges there between; and n is in particular in the range from 1 to 500, for example, from 1 to 100 and from 4 to 25, including all values and subranges there between; X is preferably a linear or branched alkylene chain containing from 1 to 30 carbon atoms and in particular 3 to 10 carbon atoms, and Y is preferably an alkylene chain that is linear or branched or that possibly comprises rings and/or unsaturations, containing from 1 to 40 carbon atoms, including from 1 to 20 carbon atoms and from 2 to 6 carbon atoms, including all values and subranges there between, for example, 6 carbon atoms.

In formulae (III) and (IV), the alkylene group representing X or Y can optionally contain in its alkylene portion at least one of the following elements:

1) 1 to 5 amide, urea or carbamate groups,
2) a C$_5$ or C$_6$ cycloalkyl group, and
3) a phenylene group optionally substituted with 1 to 3 identical or different C$_1$ to C$_3$ alkyl groups.

In formulae (III) and (IV), the alkylene groups may also be substituted with at least one element chosen from the group consisting of:

a hydroxyl group,
a C$_3$ to C$_8$ cycloalkyl group,
one to three C$_1$ to C$_{40}$ alkyl groups,
a phenyl group optionally substituted with one to three C$_1$ to C$_3$ alkyl groups,
a C$_1$ to C$_3$ hydroxyalkyl group, and
a C$_1$ to C$_6$ aminoalkyl group.

In these formulae (III) and (IV), Y may also represent:

in which R$^5$ represents a polyorganosiloxane chain and T represents a group of formula:

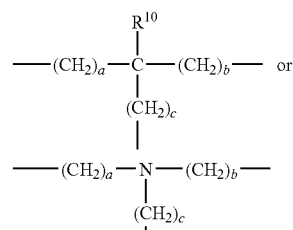

in which a, b and c are, independently, integers ranging from 1 to 10, and R$^{10}$ is a hydrogen atom or a group such as those defined for R$^1$, R$^2$, R$^3$ and R$^4$.

In formulae (III) and (IV), R$^1$, R$^2$, R$^3$ and R$^4$ preferably represent, independently, a linear or branched C$_1$ to C$_{40}$ alkyl group, preferably a CH$_3$, C$_2$H$_5$, n-C$_3$H$_7$ or isopropyl group, a polyorganosiloxane chain or a phenyl group optionally substituted with one to three methyl or ethyl groups.

As has been seen previously, the polymer may comprise identical or different moieties of formula (III) or (IV).

Thus, the polymer may be a polyamide containing several moieties of formula (III) or (IV) of different lengths, i.e. a polyamide corresponding to the formula:

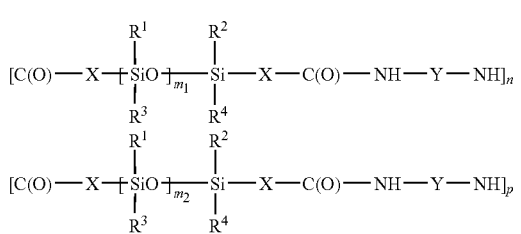
(V)

in which X, Y, n and $R^1$ to $R^4$ have the meanings given above, $m_1$ and $m_2$, which are different, are as defined above, and preferably are chosen in the range from 1 to 1 000, and p is at least one for example ranging from 2 to 500 and preferably from 2 to 200.

In this formula, the moieties may be structured to form either a block copolymer, or a random copolymer or an alternating copolymer. In this copolymer, the moieties may be not only of different lengths, but also of different chemical structures, for example containing different groups Y. In this case, the copolymer may correspond to the formula:

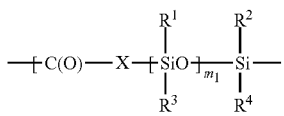
(VI)

in which $R^1$ to $R^4$, X, Y, $m_1$, $m_2$, n and p have the meanings given above and $Y^1$ is different from Y but chosen from the groups defined for Y. As previously discussed, the various moieties may be structured to form either a block copolymer, or a random copolymer or an alternating copolymer.

In an embodiment of the invention, the polyorganosiloxane-containing polymer may also contain a grafted copolymer. Thus, the polyamide containing silicone units may be grafted and optionally crosslinked with silicone chains containing amide groups. Such polymers may be synthesized with trifunctional amines.

In this case, the copolymer may comprise at least one moiety of formula:

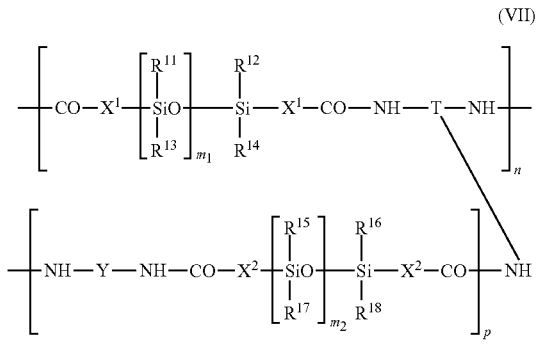
(VII)

in which $X^1$ and $X^2$, which may be identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1,000, and p is an integer of at least one, for example, p can range from 2 to 500.

In formula (VII), it is preferred that:

p is in the range from 1 to 25, including from 1 to 7, including all values and subranges there between, $R^{11}$ to $R^{18}$ are methyl groups, T corresponds to one of the following formulae:

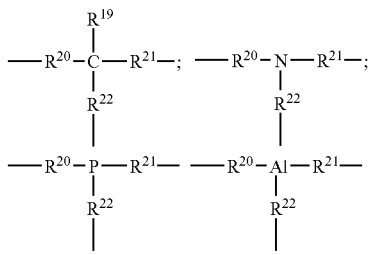

in which $R^{19}$ is a hydrogen atom or a group chosen from the groups defined for $R^1$ to $R^4$, and $R^{20}$, $R^{21}$ and $R^{22}$ are, independently, linear or branched alkylene groups, and more preferably corresponds to the formula:

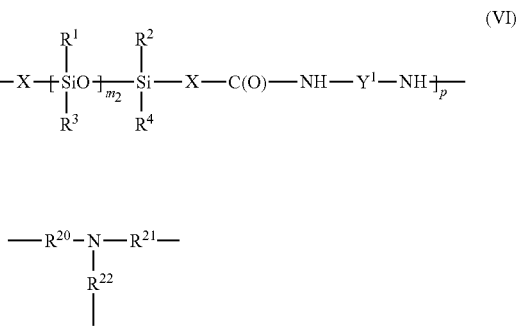

in particular with $R^{20}$, $R^{21}$ and $R^{22}$ representing —$CH_2$—$CH_2$—, $m_1$ and $m_2$ are in the range from 15 to 500, including from 15 to 45 and including all values and subranges there between, $X^1$ and $X^2$ represent —$(CH_2)_{10}$—, and Y represents —$CH_2$—.

These polyamides containing a grafted silicone moiety of formula (VII) may be copolymerized with polyamide-silicones of formula (II) to form block copolymers, alternating copolymers or random copolymers. The weight percentage of grafted silicone moieties (VII) in the copolymer may range from 0.5% to 30% by weight.

According to the invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to the invention, the preferred siloxane-based polyamides are:

polyamides of formula (III) in which m is from 15 to 300, for example, 15 to 100, including all values and subranges there between;

mixtures of two or more polyamides in which at least one polyamide has a value of m in the range from 15 to 50, including all values and subranges there between and at least one polyamide has a value of m in the range from 30 to 300, including all values and subranges there between;

polymers of formula (V) with $m_1$ chosen in the range from 15 to 50 and $m_2$ chosen in the range from 30 to 500 with the portion corresponding to $m_1$ representing 1% to 99% by weight of the total weight of the polyamide and the corresponding portion $m_2$ representing 1% to 99% by weight of the total weight of the polyamide;

mixtures of polyamide of formula (III) combining
1) 80% to 99% by weight of a polyamide in which n is equal to 2 to 10 and in particular 3 to 6, and
2) 1% to 20% of a polyamide in which n is in the range from 5 to 500 and in particular from 6 to 100;

polyamides corresponding to formula (VI) in which at least one of the groups Y and $Y^1$ contains at least one hydroxyl substituent;

polyamides of formula (III) synthesized with at least one portion of an activated diacid (diacid chloride, dianhydride or diester) instead of the diacid;

polyamides of formula (III) in which X represents —$(CH_2)_3$— or —$(CH_2)_{10}$—; and polyamides of formula (III) in which the polyamides end with a monofunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

According to the invention, the end groups of the polymer chain may end with:

a $C_1$ to $C_{50}$ alkyl ester group by introducing a $C_1$ to $C_{50}$ monoalcohol during the synthesis, a $C_1$ to $C_{50}$ alkylamide group by taking as stopping group a monoacid if the silicone is □,ω-diaminated, or a monoamine if the silicone is an □,ω-dicarboxylic acid.

According to one embodiment of the invention, it is possible to use a copolymer of silicone polyamide and of hydrocarbon-based polyamide, i.e. a copolymer comprising moieties of formula (III) or (IV) and hydrocarbon-based polyamide moieties. In this case, the polyamide-silicone moieties may be arranged at the ends of the hydrocarbon-based polyamide.

Polyamide-based polymers containing silicones may be produced by silylic amidation of polyamides based on fatty acid dimer. This approach involves the reaction of free acid sites existing on a polyamide as end sites, with organosiloxane-monoamines and/or organosiloxane-diamines (amidation reaction), or alternatively with oligosiloxane alcohols or oligosiloxane diols (esterification reaction). The esterification reaction requires the presence of acid catalysts, as is known in the art. It is desirable for the polyamide containing free acid sites, used for the amidation or esterification reaction, to have a relatively high number of acid end groups (for example polyamides with high acid numbers, for example from 15 to 20).

For the amidation of the free acid sites of the hydrocarbon-based polyamides, siloxane diamines with 1 to 300, more particularly 2 to 50 and for example, 2, 6, 9.5, 12, 13.5, 23 or 31 siloxane groups, may be used for the reaction with hydrocarbon-based polyamides based on fatty acid dimers. Siloxane diamines containing 13.5 siloxane groups are preferred, and the best results are obtained with the siloxane diamine containing 13.5 siloxane groups and polyamides containing high numbers of carboxylic acid end groups.

The reactions may be carried out in xylene to extract the water produced from the solution by azeotropic distillation, or at higher temperatures (about 180 to 200° C.) without solvent. Typically, the efficacy of the amidation and the reaction rates decrease when the siloxane diamine is longer, that is to say when the number of siloxane groups is higher. Free amine sites may be blocked after the initial amidation reaction of the diaminosiloxanes by reacting them either with a siloxane acid, or with an organic acid such as benzoic acid.

For the esterification of the free acid sites on the polyamides, this may be performed in boiling xylene with about 1% by weight, relative to the total weight of the reagents, of para-toluenesulphonic acid as catalyst.

These reactions carried out on the carboxylic acid end groups of the polyamide lead to the incorporation of silicone moieties only at the ends of the polymer chain.

It is also possible to prepare a copolymer of polyamide-silicone, using a polyamide containing free amine groups, by amidation reaction with a siloxane containing an acid group.

It is also possible to prepare a gelling agent based on a copolymer between a hydrocarbon-based polyamide and a silicone polyamide, by transamidation of a polyamide having, for example, an ethylene-diamine constituent, with an oligosiloxane-□,ω-diamine, at high temperature (for example 200 to 300° C.), to carry out a transamidation such that the ethylenediamine component of the original polyamide is replaced with the oligosiloxane diamine.

The copolymer of hydrocarbon-based polyamide and of polyamide-silicone may also be a grafted copolymer comprising a hydrocarbon-based polyamide backbone with pendent oligosiloxane groups.

This may be obtained, for example:

by hydrosilylation of unsaturated bonds in polyamides based on fatty acid dimers;

by silylation of the amide groups of a polyamide; or by silylation of unsaturated polyamides by means of an oxidation, that is to say by oxidizing the unsaturated groups into alcohols or diols, to form hydroxyl groups that are reacted with siloxane carboxylic acids or siloxane alcohols. The olefinic sites of the unsaturated polyamides may also be epoxidized and the epoxy groups may then be reacted with siloxane amines or siloxane alcohols.

The polyorganosiloxane containing polymers used in the composition of the invention are most preferably polymers of the polyorganosiloxane type such as those described in documents U.S. Pat. No. 5,874,069, U.S. Pat. No. 5,919,441, U.S. Pat. No. 6,051,216 and U.S. Pat. No. 5,981,680, the entire disclosures of which are hereby incorporated by reference.

According to another embodiment of the invention, the polyorganoxiloxane containing polymer is a homopolymer or a copolymer comprising urethane or urea groups.

As previously discussed, the polymer may comprise polyorganosiloxane moieties containing two or more urethane and/or urea groups, either in the backbone of the polymer or on side chains or as pendent groups.

The polymers comprising at least two urethane and/or urea groups in the backbone may be polymers comprising at least one moiety corresponding to the following formula:

$$\left[\left[\begin{array}{c}R^1\\|\\Si-O\\|\\R^3\end{array}\right]_m\begin{array}{c}R^2\\|\\Si-X-U-\overset{\displaystyle O}{\underset{\displaystyle \|}{C}}-NH-Y-NH-\overset{\displaystyle O}{\underset{\displaystyle \|}{C}}-U-X\\|\\R^4\end{array}\right]_n \quad (VIII)$$

in which $R^1$, $R^2$, $R^3$, $R^4$, X, Y, m and n have the meanings given above for formula (I), and U represents —O— or —NH—, such that:

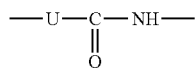

corresponds to a urethane or urea group.

In this formula (VIII), Y may be a linear or branched $C_1$ to $C_{40}$ alkylene group, optionally substituted with a $C_1$ to $C_{15}$ alkyl group or a $C_5$ to $C_{10}$ aryl group. Preferably, a —$(CH_2)_6$— group is used.

Y may also represent a $C_5$ to $C_{12}$ cycloaliphatic or aromatic group that may be substituted with a $C_1$ to $C_{15}$ alkyl group or a $C_5$ to $C_{10}$ aryl group, for example a radical chosen from the methylene-4,4-biscyclohexyl radical, the radical derived from isophorone diisocyanate, 2,4- and 2,6-tolylenes, 1,5-naphthylene, p-phenylene and 4,4'-biphenylenemethane. Generally, it is preferred for Y to represent a linear or branched $C_1$ to $C_{40}$ alkylene radical or a $C_4$ to $C_{12}$ cycloalkylene radical.

Y may also represent a polyurethane or polyurea block corresponding to the condensation of several diisocyanate molecules with one or more molecules of coupling agents of the diol or diamine type. In this case, Y comprises several urethane or urea groups in the alkylene chain.

It may correspond to the formula:

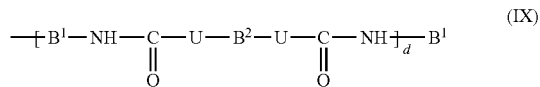

(IX)

in which $B^1$ is a group chosen from the groups given above for Y, U is —O— or —NH— and $B^2$ is chosen from:

linear or branched $C_1$ to $C_{40}$ alkylene groups, which can optionally bear an ionizable group such as a carboxylic acid or sulphonic acid group, or a neutralizable or quaternizable tertiary amine group, $C_5$ to $C_{12}$ cycloalkylene groups, optionally bearing alkyl substituents, for example one to three methyl or ethyl groups, or alkylene, for example the diol radical: cyclohexanedimethanol, phenylene groups that may optionally bear $C_1$ to $C_3$ alkyl substituents, and groups of formula:

in which T is a hydrocarbon-based trivalent radical possibly containing one or more hetero atoms such as oxygen, sulphur and nitrogen and $R^5$ is a polyorganosiloxane chain or a linear or branched $C_1$ to $C_{50}$ alkyl chain.

T can represent, for example:

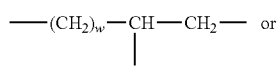

-continued

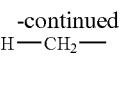

with w being an integer ranging from 1 to 10 and $R^5$ being a polyorganosiloxane chain.

When Y is a linear or branched $C_1$ to $C_{40}$ alkylene group, the —$(CH_2)_2$— and —$(CH_2)_6$— groups are preferred.

In the formula given above for Y, d may be an integer ranging from 0 to 5, preferably from 0 to 3 and more preferably equal to 1 or 2.

Preferably, $B^2$ is a linear or branched $C_1$ to $C_{40}$ alkylene group, in particular —$(CH_2)_2$— or —$(CH_2)_6$— or a group:

with $R^5$ being a polyorganosiloxane chain.

As previously discussed, the polyorganosiloxane containing polymer may be formed from silicone urethane and/or silicone urea moieties of different length and/or constitution, and may be in the form of block or random copolymers.

According to the invention, the silicone may also comprise urethane and/or urea groups no longer in the backbone but as side branches.

In this case, the polymer may comprise at least one moiety of formula:

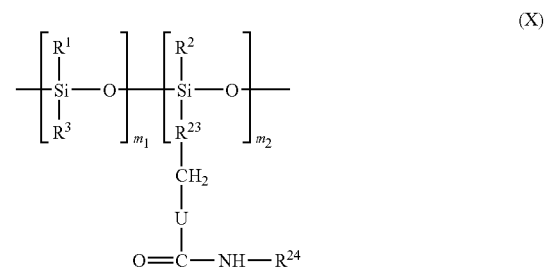

(X)

in which $R^1$, $R^2$, $R^3$, $m_1$ and $m_2$ have the meanings given above for formula (I), U represents O or NH, $R^{23}$ represents a $C_1$ to $C_{40}$ alkylene group, optionally comprising one or more hetero atoms chosen from O and N, or a phenylene group, and $R^{24}$ is chosen from linear, branched or cyclic, saturated or unsaturated $C_1$ to $C_{50}$ alkyl groups, and phenyl groups optionally substituted with one to three $C_1$ to $C_3$ alkyl groups.

The polymers comprising at least one moiety of formula (X) contain siloxane units and urea or urethane groups, and they may be used, for example, as gelling agents in the compositions of the invention.

The siloxane polymers may have a single urea or urethane group by branching or may have branches containing two urea or urethane groups, or alternatively they may contain a mixture of branches containing one urea or urethane group and branches containing two urea or urethane groups.

They may be obtained from branched polysiloxanes, comprising one or two amino groups by branching, by reacting these polysiloxanes with monoisocyanates.

As examples of starting polymers of this type containing amino and diamino branches, mention may be made of the polymers corresponding to the following formulae:

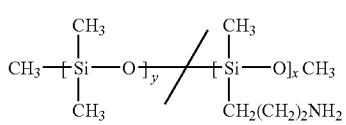

y = 57; x = 3

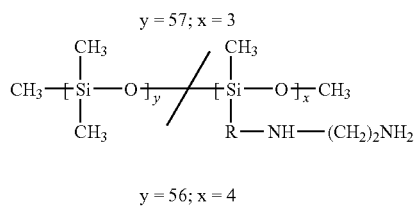

y = 56; x = 4

In these formulae, the symbol "/" indicates that the segments may be of different lengths and in a random order, and R represents a linear aliphatic group preferably containing 1 to 6 carbon atoms, including 1 to 3 carbon atoms.

Such polymers containing branching may be formed by reacting a siloxane polymer, containing at least three amino groups per polymer molecule, with a compound containing only one monofunctional group (for example an acid, an isocyanate or an isothiocyanate) to react this monofunctional group with one of the amino groups and to form groups capable of establishing hydrogen interactions. The amino groups may be on side chains extending from the main chain of the siloxane polymer, such that the groups capable of establishing hydrogen interactions are formed on these side chains, or alternatively the amino groups may be at the ends of the main chain, such that the groups capable of hydrogen interaction will be end groups of the polymer.

As a procedure for forming a polymer containing siloxane units and groups capable of establishing hydrogen interactions, mention may be made of the reaction of a siloxane diamine and of a diisocyanate in a silicone solvent so as to provide a gel directly. The reaction may be performed in a silicone fluid, the resulting product being dissolved in the silicone fluid, at high temperature, the temperature of the system then being reduced to form the gel.

The polymers that are preferred for incorporation into the compositions according to the present invention are siloxane-urea copolymers that are linear and that contain urea groups as groups capable of establishing hydrogen interactions in the backbone of the polymer.

As an illustration of a polysiloxane ending with four urea groups, mention may be made of the polymer of formula:

in which Ph is a phenyl group and n is a number larger than 0, which includes, at least 1, 2 to 500, 2 to 200, from 1 to 300, in particular from 1 to 100, and all values and subranges there between, for example 50.

This polymer is obtained by reacting the following polysiloxane containing amino groups:

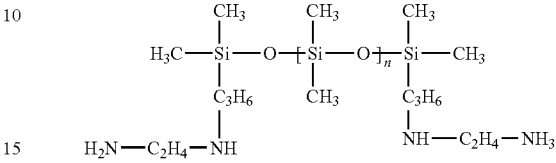

(n-50)

with phenyl isocyanate.

The polymers of formula (VIII) comprising urea or urethane groups in the chain of the silicone polymer may be obtained by reaction between a silicone containing □,ω-$NH_2$ or —OH end groups, of formula:

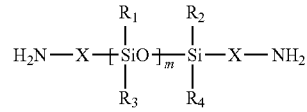

in which m, $R^1$, $R^2$, $R^3$, $R^4$ and X are as defined for formula (I) and a diisocyanate OCN—Y—NCO in which Y has the meaning given in formula (I); and optionally a diol or diamine coupling agent of formula $H_2N$—$B^2$—$NH_2$ or HO—$B^2$—OH, in which $B^2$ is as defined in formula (IX).

According to the stoichiometric proportions between the two reagents, diisocyanate and coupling agent, Y may have the formula (IX) with d equal to 0 or d equal to 1 to 5.

As in the case of the polyamide silicones of formula (II) or (III), it is possible to use in the invention polyurethane or polyurea silicones containing moieties of different length and structure, in particular moieties whose lengths differ by the number of silicone units. In this case, the copolymer may correspond, for example, to the formula:

(XI)

(Ph = Phenyl)

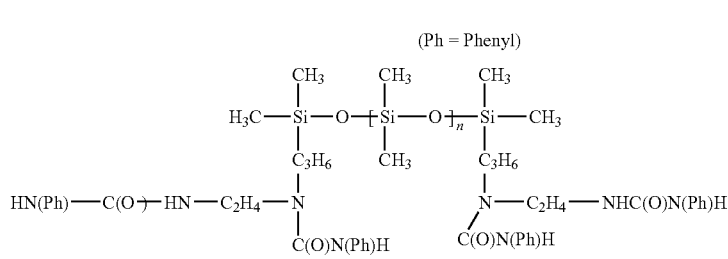

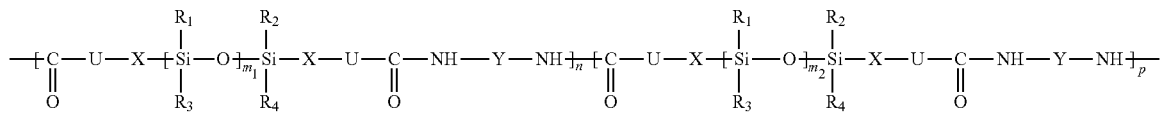

(XII)

in which $R^1$, $R^2$, $R^3$, $R^4$, X, Y and U are as defined for formula (VIII) and $m_1$, $m_2$, n and p are as defined for formula (V).

Branched polyurethane or polyurea silicones may also be obtained using, instead of the diisocyanate OCN—Y—NCO, a triisocyanate of formula:

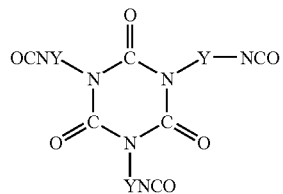

A polyurethane or polyurea silicone containing branches comprising an organosiloxane chain with groups capable of establishing hydrogen interactions is thus obtained. Such a polymer comprises, for example, a moiety corresponding to the formula:

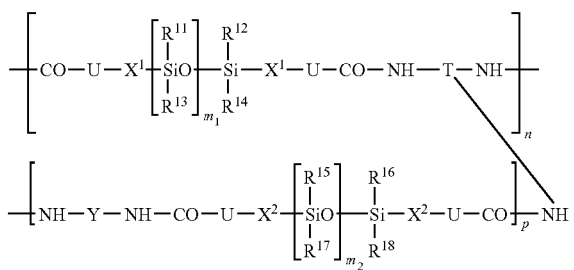

(XIII)

in which $X^1$ and $X^2$, which are identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are as defined above.

As in the case of the polyamides, this copolymer can also comprise polyurethane silicone moieties without branching.

In another embodiment of the invention, the siloxane-based polyureas and polyurethanes that are preferred are:

polymers of formula (VIII) in which m is from 15 to 300, for example, 15 to 100 and all values and subranges there between;

mixtures of two or more polymers in which at least one polymer has a value of m in the range from 15 to 50 and at least one polymer has a value of m in the range from 30 to 300, including all values and subranges there between;

polymers of formula (XII) with $m_1$ chosen in the range from 15 to 50 and $m_2$ chosen in the range from 30 to 500 with the portion corresponding to $m_1$ representing 1% to 99% by weight of the total weight of the polymer and the portion corresponding to $m_2$ representing 1% to 99% by weight of the total weight of the polymer;

mixtures of polymer of formula (VIII) combining
1) 80% to 99% by weight of a polymer in which n is equal to 2 to 10 and in particular 3 to 6, and
2) 1% to 20% of a polymer in which n is in the range from 5 to 500 and in particular from 6 to 100, copolymers comprising two moieties of formula (VIII) in which at least one of the groups Y contains at least one hydroxyl substituent;

polymers of formula (VIII) synthesized with at least one portion of an activated diacid (diacid chloride, dianhydride or diester) instead of the diacid;

polymers of formula (VIII) in which X represents —$(CH_2)_3$— or —$(CH_2)_{10}$—; and polymers of formula (VIII) in which the polymers end with a multifunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

As in the case of the polyamides, copolymers of polyurethane or polyurea silicone and of hydrocarbon-based polyurethane or polyurea may be used in the invention by performing the reaction for synthesizing the polymer in the presence of an □,ω-difunctional block of non-silicone nature, for example a polyester, a polyether or a polyolefin.

As has been seen previously, homopolymers or copolymers of the invention may contain siloxane moieties in the main chain of the polymer and groups capable of establishing hydrogen interactions, either in the main chain of the polymer or at the ends thereof, or on side chains or branches of the main chain. This may correspond to the following five arrangements:

(1)

(2)

(3)

(4)

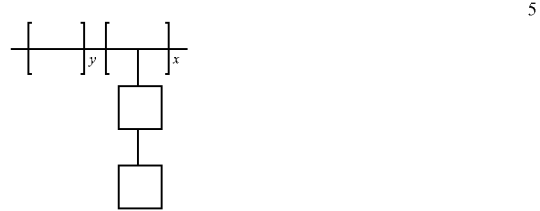

5 in which the continuous line is the main chain of the siloxane polymer and the squares represent the groups capable of establishing hydrogen interactions.

In case (1), the groups capable of establishing hydrogen interactions are arranged at the ends of the main chain.

In case (2), two groups capable of establishing hydrogen interactions are arranged at each of the ends of the main chain.

In case (3), the groups capable of establishing hydrogen interactions are arranged within the main chain in repeating moieties.

In cases (4) and (5), these are copolymers in which the groups capable of establishing hydrogen interactions are arranged on branches of the main chain of a first series of moieties that are copolymerized with moieties not comprising groups capable of establishing hydrogen interactions. Preferably, the values n, x and y are such that the polymer has the desired properties in terms of an agent for gelling fatty phases, preferably fatty phases based on silicone oil.

As examples of polymers that may be used, mention may be made of the silicone polyamides obtained in accordance with the disclosure in U.S. Pat. No. 5,981,680, the entire disclosure of which is hereby incorporated by reference.

Further examples of polyorganosiloxane containing polymers are set forth in U.S. Pat. Nos. 6,503,632 and 6,569,955, both of which are hereby incorporated by reference in their entirety.

As noted above, the polymers of the present invention can be solid or liquid at room temperature. When solid, the polymers preferably have a softening point from 50 to 130° C. Most preferably, they have a softening point ranging from 65 to 150° C., including from 70° C. to 130° C. This softening point is lower than that of other structuring polymers, which facilitates the use of the polymers that are the subject of the invention, and limits the deteriorations of the liquid fatty phase.

As noted above, the polyorganosiloxane containing polymers of the present invention contain both siloxane units and at least two groups capable of establishing hydrogen interactions such as amide linkages. The siloxane units can provide compatibility with a silicone fluid, if present, (for example with the cyclomethicones), while the groups capable of establishing hydrogen interactions and the spacing and selection of the locations of the amide linkages can facilitate gelation and the formation of cosmetic products.

According to preferred embodiments, the polyorganosiloxane-containing polymer is present in the composition in an amount effective to provide transfer resistant properties to the composition. Preferably, the polyorganosiloxane-containing polymer also provides at least one of the following properties to the composition: pliability, softness, wearing comfort, flexibility, adherence and non-tackiness.

In the compositions, the polyorganosiloxane-containing polymers are preferably present in an amount of 0.1-80 percent by weight, more preferably from 0.5 to 30 percent by weight, even more preferably from 5 to 25 percent by weight and most preferably from 10 to 20 percent by weight of the total weight of the composition. One of ordinary skill in the art will recognize that the polyorganosiloxane-containing polymer may be commercially available, and may come from suppliers in the form of a dilute solution. In such case, the amounts of the polyorganosiloxane-containing polymer disclosed herein therefore reflect the weight percent of active material. All numerical ranges and subranges are included within the numerical ranges identified above.

Volatile Non-Silicone Oil

According to preferred embodiments of the present invention, the composition comprises at least one volatile non-silicone oil. Any suitable volatile non-silicone oil can be used. The volatility of the oils can be determined using the evaporation speed as set forth in U.S. Pat. No. 6,338,839, hereby incorporated by reference.

According to preferred embodiments, suitable volatile non-silicone oils include but are not limited to volatile hydrocarbon oils, volatile alcohols, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate and their mixtures. Preferably, the volatile non-silicone oils have a flash point of at least 40° C.

Non-limiting examples of volatile non-silicone volatile oils are given in Table 1 below.

TABLE 1

| Compound | Flash Point (° C.) |
| --- | --- |
| Isododecane | 43 |
| Isohexadecane | 102 |
| Isodecyl Neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

In the compositions, the volatile non-silicone oil is preferably present in an amount of about 0.1-80 percent by weight, more preferably from about 5 to about 60 percent by weight, even more preferably from 7 to about 50 percent by weight and most preferably from about 10 to about 40 percent by weight of the total weight of the composition. All numerical ranges and subranges are included within the numerical ranges identified above.

Alkylene Polymer Wax

According to preferred embodiments of the present invention, the composition comprises an alkylene polymer wax such as, for example, an ethylene polymer wax, a butylene polymer wax, a propylene polymer wax, etc. The alkylene polymer wax is preferably an ethylene homopolymer wax.

Preferably, the ethylene homopolymer wax has an average molecular weight of between about 200 and about 700, more preferably between about 400 and about 500, as determined by vapor pressure osmometry. Most preferably, the ethylene homopolymer wax has a melting temperature range from about 82° C. to about 91° C.

In the compositions, the alkylene polymer wax is preferably present in an amount of about 1.0 to about 30 percent by weight, more preferably from about 1.0 to about 20 percent by weight, even more preferably from about 1.0 to about 10 percent by weight of the total weight of the composition. All numerical ranges and subranges are included within the numerical ranges identified above.

According to particularly preferred embodiments, the compositions comprise at least two alkylene polymer waxes. In the embodiment where two alkylene polymer waxes are present, the weight ratio of the lower molecular weight wax (for example, PE 400) to the higher molecular weight wax (for example, PE 500) is preferably between about 30:70 to about 99:1 (weight fraction of about 0.3 to about 1.0), with the ratio of about 30:70 to about 80:20 being most preferred (weight fraction of about 0.3 to about 0.80).

Suitable ethylene homopolymers include but are not limited to those sold under the trade names "Performalene 400 ("PE 400")" and "Performalene 500 ("PE 500")," those sold under the trade names "Polywax 500", "Polywax 655", and "Polywax 1.000" by Bareco, those sold under the trade names "PE 1.500 F" and "PEW 1.555" by Langer & Co., those commercialized under the trade name "TN Wax 1.495" sold by R. T. Newey, and "AC 1702" sold by Allied Chemical. "Polywax 500", "Polywax 655", and "Polywax 1,000" are homopolymers of ethylene having molecular weights of 500, 700, and 1,000, respectively, as determined by vapor pressure osmometry.

Suitable ethylene copolymers include but are not limited to ethylene-propylene copolymers sold under the trade names "Petrolite CP-7" and "Petrolite CP-12" sold by Bareco, and the ethylene-hexene copolymers sold under the trade names "Petrolite CH-7" and "Petrolite CH-12" by Bareco. Preferably, the ethylene copolymer wax has an average molecular weight of between about 200 and about 1000, more preferably between about 400 and about 700, and most preferably between about 500 and about 700. Most preferably, the ethylene copolymer wax has a melting temperature range from about 82° C. to about 91° C.

Preferably, the total amount of wax present in the compositions of the present invention, including but not limited to alkylene polymer waxes and long-chain alcohol waxes (if present), is 50% or less based on the total weight of the composition, with between about 10% and about 50% being preferred, and between about 10% and about 20% being most preferred.

Silicone Film Forming Agents

According to preferred embodiments, the composition comprises one or more silicone film forming agents. Preferably, the at least one silicone film forming agent is a silicone resin film forming agent such as an MK or an MQ resin, or mixtures thereof.

Silicone resin nomenclature is known in the art as "MDTQ" nomenclature, whereby a silicone resin is described according to the various monomeric siloxane units which make up the polymer.

Each letter of "MDTQ" denotes a different type of unit. The letter M denotes the monofunctional unit $(CH_3)_3SiO_{1/2}$. This unit is considered to be monofunctional because the silicone atom only shares one oxygen when the unit is part of a polymer. The "M" unit can be represented by the following structure:

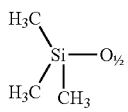

At least one of the methyl groups of the M unit may be replaced by another group, e.g., to give a unit with formula $[R(CH_3)_2]SiO_{1/2}$, as represented in the following structure:

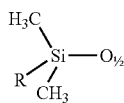

wherein R is chosen from groups other than methyl groups. Non-limiting examples of such groups other than methyl groups include alkyl groups other than methyl groups, alkene groups, alkyne groups, hydroxyl groups, thiol groups, ester groups, acid groups, ether groups, wherein the groups other than methyl groups may be further substituted.

The symbol D denotes the difunctional unit $(CH_3)_2SiO_{2/2}$ wherein two oxygen atoms bonded to the silicone atom are used for binding to the rest of the polymer. The "D" unit, which is the major building block of dimethicone oils, can be represented as:

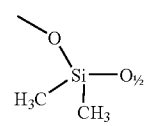

At least one of the methyl groups of the D unit may be replaced by another group, e.g., to give a unit with formula $[R(CH_3)_2]SiO_{1/2}$.

The symbol T denotes the trifunctional unit, $(CH_3)SiO_{3/2}$ and can be represented as:

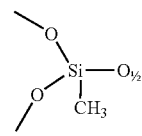

At least one of the methyl groups of the T unit may be replaced by another group, e.g., to give a unit with formula $[R(CH_3)_2]SiO_{1/2}$.

Similarly, the symbol Q denotes the tetrafunctional unit, $SiO_{4/2}$ wherein all four oxygens bonded to the silicone atom are bonded to the rest of the polymer.

Thus, a vast number of different silicone polymers can be manufactured. Further, it would be clear to one skilled in the art that the properties of each of the potential silicone polymers will vary depending on the type(s) of monomer(s), the type(s) of substitution(s), the size of the polymeric chain, the degree of cross linking, and size of any side chain(s).

Non-limiting examples of silicone polymers include silanes, siloxanes, siloxysilicates, and silsesquioxanes. A non-limiting example of such a siloxane is polydimethylsiloxane (PDMS). Polydimethylsiloxanes are generally composed of long straight chains of $(CH_3)_2SiO_{2/2}$ (i.e., D units) and have viscosities which are dependent on both the size of the polymer and the presence and nature of any substituent(s) on the polymer. A non-limiting example of a siloxysilicate is trimethylsiloxysilicate, which may be represented by the following formula:

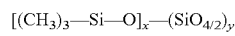

(i.e., MQ units) wherein x and y may, for example, range from 50 to 80. Silsesquioxanes, on the other hand, may be represented by the following formula:

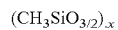

(i.e., T Units) wherein x may, for example, have a value of up to several thousand.

Polymethylsilsesquioxanes are silsesquioxanes that do not have a substituent replacing the methyl groups. Certain polymethylsilsesquioxanes have previously been used in hair care compositions. See, e.g., U.S. Pat. No. 5,246,694, the disclosure of which is incorporated herein by reference, which discloses a shampoo composition comprising a surfactant, an aqueous emulsion of highly viscous silicone in volatile silicone and a cationic polymer which is a derivative of guar gum. The highly viscous silicone disclosed therein may be chosen from silicone resins including a polymethylsilsesquioxane such as Resin MK (also called SiliconHarz MK) which is available from Wacker, and a siloxysilicate such as Resin MQ which is available from General Electric and Dow Corning.

The Resin MK and Resin MQ silicone resins may form a film after a volatile carrier has evaporated. The MQ film is generally hard and brittle at room temperature, while the MK film is generally continuous and flexible, i.e., not brittle. Depending on the application, plasticizers may be added to help obtain a more flexible, thus more comfortable, film.

In one embodiment, the silicone film former may be a polymethylsilsesquioxane film former such as Belsil PMS MK, also referred to as Resin MK, available from Wacker Chemie. This polymethylsilsesquioxane film former is a polymer comprising polymerized repeating units of $CH_3SiO_{3/2}$ (T units) and may also contain up to 1% by weight or by mole of units of the formula $(CH_3)_2SiO_{2/2}$ (D units). The weight-average molecular weight of this polymer has been estimated to be 10,000. It is believed that the polymers are in a "cage" and "ladder" configuration, as exemplified in the figures below. The majority of the polymer is in the "ladder" configuration, wherein the ends of the polymer are capped with ethoxy ($CH_3CH_2O$) groups. The ethoxy groups are generally present in an amount of 4.5% by weight and the mole percent is generally 7% (silicone units). As ethoxy groups may react with water, a small and variable amount of SiOH may also be present in the polymer.

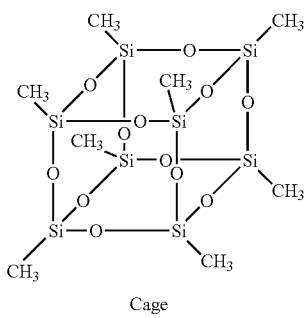

Cage

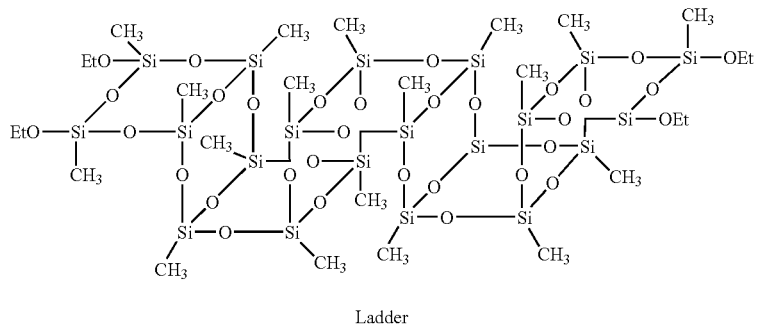

Ladder

Another non-limiting example of the at least one polymethylsilsesquioxane film former suitable for use in the present invention is KR-220L, which is available from SHIN-ETSU. This polymethylsilsesquioxane film former is composed of silicone T-units (i.e., those of formula $CH_3SiO_{3/2}$) and has Si—OH (or silanol) end units. There are no D units in KR-220L.

Other non-limiting examples of the at least one polymethylsilsesquioxane film former that may be useful in the practice of the invention include KR-242A (which is comprised of methyl T units (98%) and dimethyl D units (2%) and has Si—OH end units) and KR-251 (which is comprised of methyl T units (88%) and dimethyl D units (12%) and has Si—OH end units), both of which are available from SHIN-ETSU.

Depending on the application, the concentration of the at least one polymethylsilsesquioxane film former in the presently claimed composition may vary considerably. One of skill in the art will be able to determine routinely the amount of the at least one polymethylsilsesquioxane film former depending on the desired application.

In another embodiment, the silicone film former may be chosen from siloxysilicates. Preferably, the siloxysilicate is trimethylsiloxysilicate, which may or may not be in powder form. Trimethylsiloxysilicate (TMS) is commercially available from General Electric under the tradename SR1000 and from Wacker under the tradename TMS 803. TMS is also commercially available from Dow Chemical in a solvent, such as for example, cyclomethicone. However, according to the present invention, TMS may be used in the form of 100% active material, that is, not in a solvent.

Further non-limiting examples of the silicone film formers include silicone/(meth)acrylate copolymers, such as those as described in U.S. Pat. Nos. 5,061,481, 5,219,560, and 5,262,087, the disclosures of which are hereby incorporated by reference. Still further non-limiting examples of silicone film formers are non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the product sold under the tradename KP-545, or acrylates/stearyl acrylate/dimethicone acrylates copolymers, such as those commercially available from Shin-Etsu, for example, the product sold under the tradename KP-561, and acrylates/behenyl acrylate/dimethicone acrylates copolymer, such as those commercially available from Shin-Etsu, for example, the product sold under the tradename KP-562.

Other non-limiting examples of silicone film formers suitable for use in the present invention are silicone esters comprising units of formulae (XIV) and (XV), disclosed in U.S. Pat. Nos. 6,045,782, 5,334,737, and 4,725,658, the disclosures of which are hereby incorporated by reference:

   (XIV); and

   (XV)

wherein

R and R', which may be identical or different, are each chosen from optionally substituted hydrocarbon groups;

a and b, which may be identical or different, are each a number ranging from 0 to 3, with the proviso that the sum of a and b is a number ranging from 1 to 3, x and y, which may be identical or different, are each a number ranging from 0 to 3, with the proviso that the sum of x and y is a number ranging from 1 to 3;

$R^E$, which may be identical or different, are each chosen from groups comprising at least one carboxylic ester.

In one embodiment, $R^E$ groups are chosen from groups comprising at least one ester group formed from the reaction of at least one acid and at least one alcohol. In another embodiment, the at least one acid comprises at least two carbon atoms. In another embodiment, the at least one alcohol comprises at least ten carbon atoms. Non-limiting examples of the at least one acid include branched acids such as isostearic acid, and linear acids such as behenic acid. Non-limiting examples of the at least one alcohol include monohydric alcohols and polyhydric alcohols, such as n-propanol and branched etheralkanols such as (3,3,3-trimethylolpropoxy) propane.

Further non-limiting examples of the at least one silicone film former include liquid siloxy silicates and silicone esters such as those disclosed in U.S. Pat. No. 5,334,737, the disclosure of which is hereby incorporated by reference, such as diisostearoyl trimethylolpropane siloxysilicate and dilauroyl trimethylolpropane siloxy silicate, which are commercially available from General Electric under the tradenames SF 1318 and SF 1312, respectively.

Yet further non-limiting examples of the at least one silicone film former include polymers comprising a backbone chosen from vinyl polymers, methacrylic polymers, and acrylic polymers and at least one chain chosen from pendant siloxane groups and pendant fluorochemical groups. Non-limiting examples of such polymers comprise at least one unit derived from at least one A monomer, at least one unit derived from at least one C monomer, at least one unit derived from D monomers, and, optionally, at least one unit derived from at least one B monomer, wherein:

A, which may be identical or different, are each chosen from free-radically-polymerizable acrylic esters of at least one alcohol chosen from 1,1-dihydroperfluoroalkanols, omega-hydridofluoroalkanols, fluoroalkylsulfonamido alcohols, cyclic fluoroalkyl alcohols, and fluoroether alcohols, and analogs of any of the foregoing at least one alcohols, and free-radically-polymerizable methacrylic esters of at least one alcohol chosen from 1,1-dihydroperfluoroalkanols, omega-hydridofluoroalkanols, fluoroalkylsulfonamido alcohols, cyclic fluoroalkyl alcohols, and fluoroether alcohols, and analogs of any of the foregoing at least one alcohols;

B, which may be identical or different, are each chosen from reinforcing monomers which are copolymerizable with at least one A monomer;

C, which may be identical or different, are each chosen from monomers having the formula:

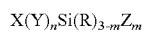

wherein

X is chosen from vinyl groups which are copolymerizable with at least one A monomer and at least one B monomer, Y is chosen from divalent allylene groups, divalent arylene groups, divalent alkarylene groups, and divalent aralkylene groups, wherein the groups comprise from 1 to 30 carbon atoms, and further wherein the groups optionally further comprise at least one group chosen from ester groups, amide groups, urethane groups, and urea groups;

n is zero or 1;

m is a number ranging from 1 to 3;

R, which may be identical or different, are each chosen from hydrogen, $C_1$-$C_4$ alkyl groups, aryl groups, and alkoxy groups; and Z, which may be identical or different, are each chosen from monovalent siloxane polymeric groups; and D, which may be identical or different, are each chosen from free-radically-polymerizable acrylate copolymers and free-radically-polymerizable methacrylate copolymers. Such polymers and their manufacture are disclosed in U.S. Pat. Nos. 5,209,924 and 4,972,037, and WO 01/32737, the disclosures of which are hereby incorporated by reference.

Other non-limiting examples of the at least one silicone film former include silicone/acrylate graft terpolymers, for example, those having the formula:

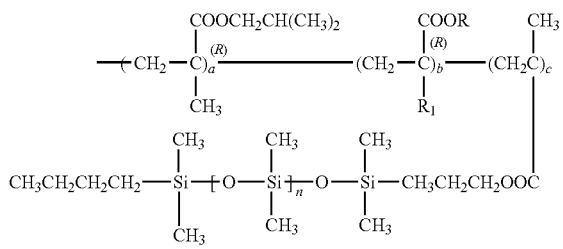

wherein a, b, and c are present in a weight ratio of 69.9:0.1:30 respectively,

R and $R_1$, which may be identical or different, are each chosen from hydrogen and $C_1$-$C_6$ alkyl groups; and m is a number ranging from 100-150.

In an embodiment, m is chosen to provide a macromer having a molecular weight ranging from 8,000 to 12,000, such as 10,000. In another embodiment, m is a number ranging from 124-135, such as 130. Non-limiting examples of these copolymers are described in WO 01/32727 A1, the disclosure of which is hereby incorporated by reference.

Still other examples of suitable silicone film formers include copolymers comprising a backbone chosen from vinyl backbones, methacrylic backbones, and acrylic polymeric backbones and further comprising at least one pendant siloxane group. Non-limiting examples of such polymers are disclosed in U.S. Pat. Nos. 4,693,935, 4,981,903, 4,981,902, the disclosures of which are hereby incorporated by reference.

In an embodiment, the at least one copolymer comprises at least one A monomer, at least one C monomer, and, optionally at least one B monomer, wherein the at least one A monomer is chosen from free-radically-polymerizable vinyl monomers, free-radically-polymerizable methacrylate monomers, and free-radically-polymerizable acrylate monomers; the at least one B monomer, if present, is chosen from at least one reinforcing monomer copolymerizable with the at least one A monomer, and the at least one C monomer is chosen from monomers having the formula:

$$X(Y)_n Si(R)_{3-m} Z_m$$

wherein:

X is chosen from vinyl groups which are copolymerizable with the at least one A monomer and with the at least one B monomer;

Y is chosen from divalent groups;

n is zero or 1;

m is a number ranging from 1 to 3;

R, which may be identical or different, are each chosen from hydrogen, optionally substituted $C_1$-$C_{10}$ alkyl groups, optionally substituted phenyl groups, and optionally substituted $C_1$-$C_{10}$ alkoxy groups; and Z, which may be identical or different, are each chosen from monovalent siloxane polymeric groups.

Non-limiting examples of A monomers include methacrylic acid esters of $C_1$-$C_{12}$ linear alcohols, methacrylic acid esters of $C_1$-$C_{12}$ of branched alcohols, styrene monomers, vinyl esters, vinyl chloride monomers, vinylidene chloride monomers, and acryloyl monomers.

Non-limiting examples of B monomers include acrylic monomers comprising at least one group chosen from hydroxyl, amino, and ionic groups, and methacrylic monomers comprising at least one group chosen from hydroxyl, amino, and ionic groups. Non-limiting examples of ionic groups include quaternary ammonium groups, carboxylate salts, and sulfonic acid salts.

The C monomers are the same as those described for the C monomers in the previous paragraphs.

Other non-limiting examples of the silicone film-former include a copolymer chosen from vinyl-silicone graft copolymers having the following formula and vinyl-silicone block copolymers having the following formula:

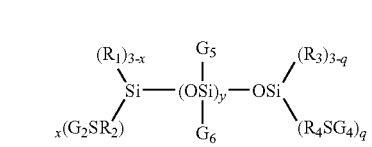

wherein $G_5$, which may be identical or different, are each chosen from alkyl groups, aryl groups, aralkyl groups, alkoxy groups, alkylamino groups, fluoroalkyl groups, hydrogen, and —ZSA groups, wherein A is chosen from vinyl polymeric segments comprising at least one polymerized free-radically-polymerizable monomer, and Z is chosen from divalent $C_1$-$C_{10}$ alkylene groups, divalent aralkylene groups, divalent arylene groups, and divalent alkoxylalkylene groups. In an embodiment Z is chosen from methylene groups and propylene groups.

$G_6$, which may be identical or different, are each chosen from alkyl groups, aryl groups, aralkyl groups, alkoxy groups, alkylamino groups, fluoroalkyl groups, hydrogen, and —ZSA groups, as defined above;

$G_2$ comprises A;

$G_4$ comprises A;

$R_1$, which may be identical or different, are each chosen from alkyl groups, aryl groups, aralkyl groups, alkoxy groups, alkylamino groups, fluoroalkyl groups, hydrogen, and hydroxyl. In one embodiment, $R_1$ is chosen from $C_1$-$C_4$ alkyl groups, such as methyl groups, and hydroxyl.

$R_2$, which may be identical or different, are each chosen from divalent $C_{1-10}$ alkylene groups, divalent arylene groups, divalent aralkylene groups, and divalent alkoxyalkylene groups. In one embodiment, $R_2$ is chosen from divalent $C_1$-$C_3$ alkylene groups and divalent $C_7$-$C_{10}$ aralkylene groups. In another embodiment, $R_2$ is chosen from —$CH_2$— groups and divalent 1,3-propylene groups.

$R_3$, which may be identical or different, are each chosen from alkyl groups, aryl groups, aralkyl groups alkoxy groups, alkylamino groups, fluoroalkyl groups, hydrogen, and hydroxyl. In one embodiment, $R_3$ is chosen from $C_1$-$C_4$ alkyl groups and hydroxyl. In another embodiment, $R_3$ is chosen from methyl groups.

$R_4$, which may be identical or different, are each chosen from divalent $C_1$-$C_{10}$ alkylene groups, divalent arylene groups, divalent aralkylene groups, and divalent alkoxyalkylene groups. In one embodiment, $R_4$ is chosen from divalent $C_1$-$C_3$ alkylene groups and divalent $C_7$-$C_{10}$ aralkylene groups. In another embodiment, $R_4$ is chosen from divalent —$CH_2$— groups and divalent 1,3-propylene groups.

x is a number ranging from 0 to 3;

y is a number greater than or equal to 5. In an embodiment, y ranges from 10 to 270, and in another embodiment, y ranges from 40 to 270.

q is a number ranging from 0 to 3;

Non-limiting examples of these polymers are described in U.S. Pat. No. 5,468,477, the disclosure of which is hereby incorporated by reference. A non-limiting example of such polymers is poly(dimethylsiloxane)-g-poly(isobutyl methacrylate), which is commercially available from 3M Company under the tradename VS 70 IBM.

According to preferred embodiments, the silicone film former is present in the composition in an amount ranging from 0.1% to 30% by weight relative to the total weight of the composition. Preferably, the silicone film former is present in an amount ranging from 0.5% to 20% by weight relative to the total weight of the composition, and more preferably from 1% to 10%. One of ordinary skill in the art will recognize that the silicone film former of the present invention may be commercially available, and may come from suppliers in the form of a dilute solution. The amounts of the silicone film former disclosed herein therefore reflect the weight percent of active material.

Coloring Agent

The composition of the present invention may optionally contain at least one coloring agent. According to preferred embodiments of the present invention, the composition further comprises at least one coloring agent.

In the composition, any coloring agent can be used. The at least one coloring agent is preferably chosen from pigments, dyes such as liposoluble dyes, nacreous pigments, and/or pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, most preferably from 0.0001% to 6%.

The nacreous pigments which may be used according to the present invention include but are not limited to nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, may be present in the composition in a concentration ranging up to 50% by weight of the total weight of the composition, such as from 0.1% to 20%, preferably from 0.1% to 15%.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 1% to 30%, and further such as from 1% to 15%.

Long-Chain Alcohol Wax

The composition of the present invention may optionally contain at least one long-chain alcohol wax. According to preferred embodiments of the present invention, the composition further comprises at least one long-chain alcohol wax. It is believed that the long-chain wax helps improve, among other things, the hardness of solid compositions.

Preferably, the at least one long-chain alcohol wax has an average carbon chain length of between about 20 and about 60 carbon atoms, most preferably between about 30 and about 50 carbon atoms. Suitable examples of long-chain alcohol waxes include but are not limited to alcohol waxes commercially available from Baker Hughes under the Performacol trade name such as, for example, Performacol 350, 425 and 550. Most preferably, the long-chain alcohol wax has a melting temperature range from about 93° C. to about 105° C.

According to preferred embodiments, the long-chain alcohol wax is present in the composition in an amount ranging from 0.1% to 50% by weight relative to the total weight of the composition. Preferably, the long-chain alcohol wax is present in an amount ranging from 0.1% to 20% by weight relative to the total weight of the composition, and more preferably from 0.1% to 10%. One of ordinary skill in the art will recognize that the long-chain alcohol wax of the present invention may be commercially available, and may come from suppliers in the form of a dilute solution. The amounts of the long-chain alcohol wax disclosed herein therefore reflect the weight percent of active material.

According to particularly preferred embodiments, the weight fraction of long-chain alcohol wax to ethylene polymer wax is from about 0.005 to about 0.1 (that is, about 0.5:99.5 to about 10:90 ratio of long-chain alcohol wax to ethylene polymer wax(es)), with about 0.01 to about 0.03 being most preferred.

Volatile Silicone Oil

The composition of the present invention may optionally contain at least one volatile silicone oil. According to preferred embodiments of the present invention, the composition further comprises at least one volatile silicone oil. According to particularly preferred embodiments, the composition further comprises at least one cyclic volatile silicone oil.

Suitable volatile silicone oils include but are not limited to linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |

TABLE 1-continued

| Compound | Flash Point (° C.) | Viscosity (cSt) |
|---|---|---|
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 St) from Dow Corning | 102 | 3 |

If present, the volatile silicone oil is preferably present in an amount of about 0.1-80 percent by weight, more preferably from about 5 to about 60 percent by weight, even more preferably from 5 to about 50 percent by weight and most preferably from about 5 to about 20 percent by weight of the total weight of the composition. All numerical ranges and subranges are included within the numerical ranges identified above.

The compositions of the invention can also optionally comprise any additive usually used in such compositions. For example, oils, organogelators, dispersants, antioxidants, vitamins, emollients, preserving agents, fragrances, waxes, fillers, neutralizing agents, cosmetic and dermatological active agents, moisturizers, humectants, water, sunscreen agents, gelling agents, elastomers, short chain esters, surfactants, plasticizers, and mixtures thereof can be added, if desired. Further examples of suitable optional components can be found in the references which have been incorporated by reference in this application. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the compositions, kits and methods according to the invention are not, or are not substantially, adversely affected by the envisaged addition.

Such additives may be present in the composition in a proportion from 0% to 90% relative to the total weight of the composition, preferably from 0.01% to 85%, and most preferably from 10 to 80% (if present).

Specific examples of acceptable optional ingredients include but are not limited to non-volatile silicone oils such as, for example, non-volatile linear polydimethylsiloxanes (PDMSs) such as dimethicones; polydimethylsiloxanes comprising alkyl, alkoxy or phenyl groups, which are pendent and/or at the end of a silicone chain, these groups each containing from 2 to 24 carbon atoms; and phenylated silicones, for instance phenyl trimethicones, phenyl dimethicones, phenyl trimethylsiloxydiphenylsiloxanes, diphenyl dimethicones, diphenyl methyldiphenyl trisiloxanes and 2-phenylethyl tri methylsiloxysilicates.

Suitable non-silicone, non-volatile oils include but are not limited to polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol; and mixtures thereof.

Suitable elastomers include but are not limited to crosslinked elastomeric polyorganosiloxane which can bear hydrophile groups, such as polyoxyethylene or copoly(oxyethylene/oxypropylene), if desired. Such elastomeric silicones may also optionally have hydrophile groups in the crosslinking chain.

Suitable crosslinked elastomeric polyorganosiloxanes include, but are not limited to, the crosslinked elastomeric polyorganosiloxanes described in application EP-A-0,295,886, the disclosure of which is incorporated herein by reference. According to that application, the elastomers are obtained by addition reaction and crosslinking, in the presence of a platinum-type catalyst, of at least:

(a) a polyorganosiloxane having at least two $C_2$ to $C_6$ lower alkenyl groups per molecule; and (b) a polyorganosiloxane having at least two hydrogen atoms linked to a silicon atom per molecule.

Suitable elastomers also include but are not limited to those described in U.S. Pat. No. 5,266,321, the disclosure of which is incorporated by reference herein. According to that patent, the elastomers are chosen in particular from:

i) polyorganosiloxanes comprising $R_2SiO$ and $RSiO_{1.5}$ units and optionally $R_3SiO_{0.5}$ and/or $SiO_2$ units in which the radicals R, independently of each other, are chosen from a hydrogen, an alkyl such as methyl, ethyl or propyl, an aryl such as phenyl or tolyl, an unsaturated aliphatic group such as vinyl, the weight ratio of the units $R_2SiO$ to the units $RSiO_{1.5}$ ranging from 1/1 to 30/1;

ii) polyorganosiloxanes which are insoluble and swellable in silicone oil, obtained by addition of an polyorganohydrogenosiloxane (1) and of a polyorganosiloxane (2) having unsaturated aliphatic groups such that the amount of hydrogen or of unsaturated aliphatic groups in (1) and (2) respectively ranges from 1 to 20 mol % when the polyorganosiloxane is non-cyclic and from 1 to 50 mol % when the polyorganosiloxane is cyclic. Optionally, these polyorganosiloxanes can comprise from 1 to 40 oxyalkylene groups, such as oxypropylene and/or oxyethylene groups.

Specific examples of elastomeric polyorganosiloxanes which can be used according to the invention include those sold or made under the names KSG6 from Shin-Etsu, Trefil E-505C, Trefil E-506C, DC 9506 or DC 9701 from Dow-Corning, Gransil from Grant Industries (SR-CYC, SR DMF10, SR-DC556) or those marketed in the form of pre-constituted gels (DC9040, DC9041 from Dow Corning, KSG15, KSG17, KSG16, KSG18, KSG21 from Shin-Etsu, Gransil SR 5CYC gel, Gransil SR DMF 10 gel, Gransil SR DC556 gel, SF 1204 and JK 113 from General Electric) or emulsifying elastomers such as those sold under the names of KSG-210, KSG-30, KSG-31, KSG-32, KSG-33, KSG-40, KSG 41, KSG-42, KSG-43, KSG-44 and KSG-710 from Shin-Etsu, or coated elastomers such as products sold under the denomination KSP (for example, KSP100, KSP 200, KSP 300) sold by Shin Etsu and/or those described in U.S. Pat. No. 5,538,793, the disclosure of which is hereby incorporated by reference. A mixture of these commercial products may also be used.

If present, the elastomeric compounds are preferably present in an amount of 0.1-25 percent by weight, more preferably from 0.5 to 20 percent by weight, even more preferably from 1 to 15 percent by weight and most preferably from 3 to 10 percent by weight of the total weight of the composition. One of ordinary skill in the art will recognize that the elastomeric compound may be commercially available, and may come from suppliers in the form of a dilute solution. In such case, the amounts of the elastomer disclosed herein therefore reflect the weight percent of active material. All numerical ranges and subranges are included within the numerical ranges identified above.

The composition according to the invention can be in the form of a tinted or non tinted dermatological composition or a care composition for keratin materials such as the skin, the hair, the lips and/or superficial body growths, in the form of an antisun composition or make-up-removing product in stick form. It can be used in particular as a care base for the skin, superficial body growths or the lips (lip balms, for protecting the lips against cold and/or sunlight and/or the wind, or care cream for the skin, the nails or the hair).

The composition of the invention may also be in the form of a colored make-up product for the skin, in particular a foundation, optionally having care or treating properties, a blusher, a face powder, an eye shadow, a concealer product, an eyeliner, a make-up product for the body; a make-up product for the lips such as a lipstick, optionally having care or treating properties; a make-up product for superficial body growths such as the nails or the eyelashes, in particular in the form of a mascara cake, or for the eyebrows and the hair, in particular in the form of a pencil.

Needless to say, the composition of the invention should be cosmetically or dermatologically acceptable, i.e., it should contain a non-toxic physiologically acceptable medium and should be able to be applied to the skin, superficial body growths or the lips of human beings. For the purposes of the invention, the expression "cosmetically acceptable" means a composition of pleasant appearance, odor, feel and/or taste.

According to preferred embodiments of the present invention, methods of treating, caring for and/or making up keratinous material such as skin, lips, hair and mucous membranes by applying compositions of the present invention to the keratinous material in an amount sufficient to treat, care for and/or make up the keratinous material are provided.

According to other preferred embodiments, methods of covering or hiding defects associated with keratinous material such as imperfections or discolorations by applying compositions of the present invention to the keratinous material in an amount sufficient to cover or hide such defects are provided.

According to yet other preferred embodiments, methods of enhancing the appearance of keratinous material by applying compositions of the present invention to the keratinous material in an amount sufficient to enhance the appearance of the keratinous material are provided.

In accordance with the three preceding preferred embodiments, the compositions of the present invention are applied topically to the desired area of the skin in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once or twice daily, more preferably once daily and then preferably allowed to dry before subjecting to contact such as with clothing or other objects. The composition is preferably applied to the desired area that is dry or has been dried prior to application.

According to a preferred embodiment of the present invention, compositions having improved cosmetic properties such as, for example, improved long wear, transfer resistance or waterproof properties are provided. The improved properties may also be chosen from improved flexibility, wearability, drying time or retention as well as reduced tackiness or migration over time.

In accordance with yet another embodiment of the present invention, kits comprising a composition comprising at least one polyorganosiloxane-containing polymer, at least one volatile non-silicone oil, at least one ethylene polymer wax, at least one silicone film-forming agent and, optionally, at least one long-chain alcohol wax, at least one coloring agent, and/or at least one volatile silicone oil are provided. In addition to this composition, the kits of the present invention can further comprise one or more compositions such as, for example, compositions to be applied on top of make-up compositions (for example, glosses or topcoats), compositions to be applied underneath make-up compositions (for example, primers or basecoats), and compositions for removing make-up from keratin materials. Any suitable topcoat, basecoat or removal composition can be included in such kits.

The packaging and application device for any such kit or compositions in the kit may be chosen and manufactured by persons skilled in the art on the basis of their general knowledge, and adapted according to the nature of the compositions to be packaged. Indeed, the type of device to be used can be in particular linked to the consistency of the composition, in particular to its viscosity; it can also depend on the nature of the constituents present in the compositions.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Example 1

Sample Compositions

| Seq | Trade Name | INCI Name | Composition A % w/w | Composition B % w/w | Composition C % w/w | Composition D % w/w | Composition E % w/w |
|---|---|---|---|---|---|---|---|
| A | PERMETHYL 99A | ISODODECANE | 36.62 | 33.12 | 21.62 | 18.40 | 29.40 |
|  | DC245 | Cyclopentasiloxane | 0.00 | 0.00 | 15.00 | 13.00 | 0.00 |
|  | SR 1000 | trimethylsyloxysilicate | 11.80 | 12.30 | 11.80 | 12.32 | 12.32 |
|  | DC 2-8179 GELLANT- BATCH # PE02121867 | NYLON-611/DIMETHICONE COPOLYMER | 10.00 | 12.50 | 10.00 | 12.70 | 12.70 |
|  |  |  | 58.42 | 57.92 | 58.42 | 56.42 | 54.42 |
| C | Red Iron Oxide | Iron Oxides | 0.58 | 0.58 | 0.58 | 0.58 | 0.58 |
|  | yellow 5 Al Lake | yellow 5 Al lake | 0.66 | 0.66 | 0.66 | 0.66 | 0.66 |
|  | FDC yellow 6 Al Lake | yellow 6 | 0.64 | 0.64 | 0.64 | 0.64 | 0.64 |
|  | DC Red 7 W | Red 7 Lake | 0.78 | 0.78 | 0.78 | 0.78 | 0.78 |
|  | blue 1 lake | blue 1 | 0.06 | 0.06 | 0.06 | 0.06 | 0.06 |
|  | black iron oxide | Iron Oxides | 0.14 | 0.14 | 0.14 | 0.14 | 0.14 |
|  | titanium dioxide | titanium dioxide | 0.77 | 0.77 | 0.77 | 0.77 | 0.77 |
|  | Bentone gel ISD V | DISTEARDIMONIUM HECTORITE/isododecane/propylene carbonate 10/87/3 | 10.00 | 10.00 | 10.00 | 10.00 | 10.00 |
|  | SR 1000 | trimethylsyloxysilicate | 3.20 | 3.20 | 3.20 | 3.20 | 3.20 |
|  | PERMETHYL 99A | ISODODECANE | 5.25 | 5.25 | 5.25 | 5.25 | 5.25 |
|  |  |  | 22.08 | 22.08 | 22.08 | 22.08 | 22.08 |
| D | Gemtone Ruby G 010 | Mica and Titanium dioxide and Iron oxides and Carmine | 4.50 | 4.50 | 4.50 | 4.50 | 4.50 |
|  | Sunsphere Silica | Silica | 0.00 | 2.00 | 0.00 | 2.00 | 2.00 |
|  | Beady bead | Aluminium Calcium Sodium Silicate | 0.00 | 2.00 | 0.00 | 0.00 | 2.00 |
|  | MICA CONCORD 1000 m | MICA | 0.00 | 0.00 | 0.00 | 2.00 | 2.00 |
|  |  |  | 4.50 | 8.50 | 4.50 | 8.50 | 10.50 |
| B | Performalene 400 | polyethylene | 6.00 | 6.00 | 6.00 | 5.20 | 5.20 |
|  | Polywax500 | polyethylene | 9.00 | 4.50 | 9.00 | 7.80 | 7.80 |
|  | performacol 550 alcohol | C30-50 alcohols | 0 | 1.00 | 0 | 0.00 | 0.00 |
|  |  |  | 15.00 | 11.50 | 15.00 | 13.00 | 13.00 |
|  |  |  | 100.00 | 100.00 | 100.00 | 100.00 | 100.00 |
|  |  | HARDNESS (g) | 33 | 68 | 52 | 61 | 53 |
|  |  | Wear | 80 | 75 | 73 | 84 | 90 |

Procedure of Preparing compositions
1. Combine Phase A ingredients together, then transfer to the beaker to a 100° C. oil bath and mix with a propeller mixer until the solution completely uniform.
2. Combine Phase B ingredients together into Phase A, then mix until the waxes melted.
3. Add Phase C ingredients into Phase (A+B) solution and mix for about 10 minutes with high speed of mixer rotation.

darkness or intensity of the color. The panelists were then asked to eat a meal consisting of a sandwich, a salad and a hot beverage. The lips of the panelists were photographed after the meal using the device above, and the images analyzed for L* color value. The wear is reported as % wear and indicates how much of the composition remains on the lips.

Example 2

| Seq | Trade Name | INCI Name | Composition F | Composition G |
|---|---|---|---|---|
| A | PERMETHYL 99A | ISODODECANE | 12.00 | 12.00 |
|  | DC 245 Fluid | Cyclopentasiloxane | 18.02 | 15.61 |
|  | SR 1000 | trimethylsyloxysilicate | 6.00 | 8.00 |
|  | DC 2-8179 GELLANT-BATCH # 2121867 | NYLON-611/DIMETHICONE COPOLYMER | 2.57 | 3.48 |
|  | PERFORMAL 400 | polyethylene | 5.20 | 4.80 |
|  | Polywax500 | polyethylene | 1.20 | 1.10 |
| B | MT-100-Z | TITANIUM DIOXIDE + STEARIC ACID + ALUMINUM HYDROXIDE (74/13/13 | 5.50 | 5.50 |
|  | ITT-Titanium Dioxide | ITT-Titanium Dioxide | 7.54 | 7.54 |
|  | ITT-Iron Oxide - Yellow | ITT-Iron Oxides | 2.06 | 2.06 |
|  | ITT-Iron Oxide - Red | ITT-Iron Oxides (and) Iron Oxides | 0.72 | 0.72 |
|  | ITT-Iron Oxide - Blue | ITT-Iron Oxides (and) ULTRAMARINE | 0.68 | 0.68 |
|  | DC 245 Fluid | Cyclopentasiloxane | 26.40 | 26.40 |
|  | DC 9701 powder | DIMETHICONE CROSSPOLYMER/silica | 1.10 | 1.10 |
|  | pigment paste 577-52-5 |  | 44.00 | 44.00 |
| C | LUXSIL | CALCIUM SODIUM BOROSILICATE | 7.00 | 7.00 |
|  | GANZPEARL GMP 0820 | METHYL METHACRYLATE CROSSPOLYMER | 3.50 | 3.50 |
|  | Sunsphere Silica | SILICA | 0.50 | 0.50 |
|  |  | total = | 100.00 | 100.00 |

4. Add phase D into phase (A+B+C) and mix with high speed for 15 minutes.
5. Reduce temperature down to 90-95° C., continue mixing at low speed, for 5-10 minutes
6. Transfer the resulting fluid to the mold at room temperature.
7. After cool at room temperature about 10 minutes, put the mold in the freezer for 40 minutes.

Procedure of Preparing Phase C (Color Grind)
1. Combine Phase C ingredients together, then mix by hand until pigments are totally wet, then use high speed mixer to mix about 10 minutes.
2. Transfer the mixture to the Disconti-Mill and mill for 1 hour until the color grind becomes homogeneous.
3. Transfer the color grind phase C into the container for use in the procedure above.

Procedure for Determining Hardness
The procedure used for determining hardness is set forth herein above.

Procedure for Determining Wear
The lip compositions were applied to the lips of 6 panelists. The lips were photographed before, and immediately after, application using diffuse lighting in a device such as the one described and claimed in US20030067545, the entire contents of which are incorporated by reference, and the images analyzed for L* color value. The L* color value indicates the Procedure of Preparing Compositions
The compositions were prepared using the same procedures as set forth in example 1, except that step 4 was omitted.

What is claimed is:
1. A solid composition comprising Nylon-611/dimethicone copolymer, isododecane, ethylene homopolymer wax having an average molecular weight of between about 400 and about 700, long-chain alcohol wax having an average carbon chain length of between about 30 and about 50 carbon atoms, a crosslinked elastomeric polyorganosiloxane comprising a hydrophilic group that is polyoxyethylene, and two silicone resin film forming agents that are a siloxysilicate and a polydimethyl siloxane
    wherein the Nylon-611/dimethicone copolymer is present in an amount of 0.1 to 10% by weight of the composition,
    the long chain alcohol wax is present in an amount of 0.1 to 10% by weight of the composition,
    the ethylene homopolymer wax is present in an amount of about 1 to about 10%,
    the isododecane is present in an amount of from 10 to 40% by weight,
    the crosslinked elastomeric polyorganosiloxane comprising a hydrophilic group that is polyoxyethylene is present in an amount of from 3 to 10% by weight of the composition, and
    the siloxysilcate and the polydimethyl siloxane are present in an amount of 1 to 10% by weight of the composition.

2. The composition according to claim 1, wherein the composition further comprises at least one coloring agent.

3. The composition according to claim 1, further comprising at least one volatile silicone oil.

4. The composition according to claim 1, further comprising at least one cyclic volatile silicone oil.

5. The composition according to claim 1, in the form of a lipstick.

6. The composition according to claim 1, in the form of a foundation.

* * * * *